United States Patent [19]

McCollum

[11] Patent Number: 4,608,201

[45] Date of Patent: Aug. 26, 1986

[54] PROCESS FOR PREPARING LACTAM IMIDES

[75] Inventor: Gregory J. McCollum, Glenshaw, Pa.

[73] Assignee: PPG Industries, Inc., Pittsburgh, Pa.

[21] Appl. No.: 612,213

[22] Filed: May 21, 1984

[51] Int. Cl.$^4$ .................. C07D 201/02; C07D 201/08
[52] U.S. Cl. ...................................... 540/529; 540/451; 546/245; 548/530; 548/538
[58] Field of Search .................. 260/239.3 R, 239.3 A

[56] References Cited

U.S. PATENT DOCUMENTS

| | | | |
|---|---|---|---|
| 3,865,814 | 2/1975 | Lüssi et al. | 260/239.3 R |
| 3,988,318 | 10/1976 | Copes et al. | 260/239.3 R |
| 4,221,789 | 9/1980 | Rodriguez et al. | 260/239.3 R |

FOREIGN PATENT DOCUMENTS 1102521  3/1968  United Kingdom .

*Primary Examiner*—John Kight
*Assistant Examiner*—Nathan M. Nutter
*Attorney, Agent, or Firm*—Linda Pingitore

[57] ABSTRACT

A process for preparing a lactam imide involves reacting together a lactam, a non-volatile carboxyl group-containing material, and an anhydride of a volatile carboxylic acid with the proviso that an appreciable amount of non-volatile carboxyl group-containing material and volatile carboxylic acid which is generated as the anhydride reacts are both present in the reaction mixture at the same time.

10 Claims, No Drawings

PROCESS FOR PREPARING LACTAM IMIDES

BACKGROUND OF THE INVENTION

The present invention relates to a method for preparing lactam imides which are useful as initiators for anionic polymerization of lactams.

In G.B. No. 1,102,521 there is disclosed a method of producing N-acyl caprolactams and di-acyl bis-caprolactams by reacting a carboxylic acid, preferably a dicarboxylic acid, with acetyl caprolactam. This process, however, is economically disadvantageous as well as being inefficient because the preparation and isolation of N-acetyl caprolactam requires a separate process step. That is, first one must react epsilon-caprolactam with acetic anhydride. The acetic acid which is eliminated as the reaction proceeds is removed by distillation. Only after this step is completed and the N-acetyl caprolactam is formed and isolated can one proceed to prepare the N-acyl caprolactam by reacting the N-acetyl caprolactam with carboxylic acid. There is a need, therefore, for a more efficient and versatile process which can be performed in one step without the need for isolating intermediate products and which can be used to prepare a variety of lactam imides.

SUMMARY OF THE INVENTION

In accordance with the present invention there is provided a process for preparing a lactam imide which comprises reacting together a lactam, a non-volatile carboxyl group-containing material, and an anhydride of a volatile carboxylic acid, with the proviso that an appreciable amount of non-volatile carboxyl group-containing material and volatile carboxylic acid which is generated as the anhydride reacts are both present in the reaction mixture at the same time. The present invention also relates to the product prepared by the aforesaid process.

DETAILED DESCRIPTION OF THE INVENTION

The process for preparing lactam imides of the present invention can be carried out in one stage without intervening steps and without the necessity of isolating intermediate reaction products. The process comprises reacting together a lactam, a non-volatile carboxyl group-containing material, and anhydride of a volatile carboxylic acid. A fundamental aspect of this process resides in the proviso that an appreciable amount of non-volatile carboxyl group-containing material and volatile carboxylic acid which is generated as the anhydride reacts are both present in the reaction mixture at the same time. By an appreciable amount is meant at least 5 mole percent. The process provides a convenient and efficient method of converting carboxyl group-containing materials to initiators for anionic lactam polymerization.

The lactam monomer can be selected from a variety of materials represented by the following structural formula:

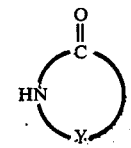

wherein Y is a $C_3$ to $C_{12}$ alkylene radical. Examples of suitable lactams include lauryl lactam, epsilon-caprolactam, valerolactam, 2-pyrrolidinone, and 2-azocyclotridecanone. Preferably epsilon-caprolactam is utilized.

The anhydride should be of a volatile carboxylic acid so that its boiling point readily permits removal at elevated temperature, typically within the range of from about 100° C. to about 250° C. and reduced pressures of from 760 millimeters to 10 millimeters of mercury. The anhydride preferably contains at least four carbon atoms. Anhydrides with more than 12 carbon atoms are not preferred because they are not as volatile. Acetic anhydride is a preferred material.

The non-volatile carboxyl group-containing material can be chosen from a large variety of materials both monomeric and polymeric. Moreover the monomeric or polymeric material can be either a moncarboxylic acid or polycarboxylic acid. In one preferred embodiment the non-volatile carboxyl group-containing material is a monocarboxylic acid having at least four carbon atoms. Examples of suitable monocarboxylic acids include butyric acid, hexanoic acid and lauric acid. More preferably the non-volatile carboxyl group-containing material is a polycarboxylic acid containing at least two carbon atoms. Suitable examples include adipic acid, glutaconic acid, pimelic acid, terephthalic acid, azelaic acid, isophthalic acid and dimerized fatty acids such as those commercially available from Emery Industries under the trademark designation EMPOL. Terephthalic acid, azelaic acid and isophthalic acid are preferably utilized.

Most preferred, the non-volatile carboxyl group-containing material is a carboxyl functional polymer having an end group calculated molecular weight of at least 300. Use of these materials results in polymeric initiators which can be advantageously utilized to modify a lactam polymer during anionic polymerization. The most preferred polymers are essentially hydrocarbon polymers because since they are hydrophobic in nature they help to lower water absorption of the polylactam. The most preferred materials for use in the present invention are carboxyl-terminated polybutadienes and carboxyl-terminated polybutadiene acrylonitrile copolymers. Lactam imide initiators prepared according to the claimed process and utilizing these polymers have been found to impart both lower water absorption and good impact resistance to polycaprolactam which has been modified with these materials. Other suitable polymeric materials include carboxy-terminated polyesters such as poly(12-hydroxystearic acid) and a polyester prepared from azelaic acid and polypropylene glycol.

The lactam imide of the desired carboxyl functional material which is prepared by the one step transacylation reaction of the present invention, when used as an initiator for anionic polymerization of lactams, results in more efficient production of polylactam. The initiators which are prepared by this process, both polymeric and monomeric can be prepared in advance of use, isolated and stored. The initiator compositions are essentially free of contaminating materials normally present in a composition prepared in-situ, for example, basic catalyst and non-polymeric initiator. Previously, polymeric initiators had to be prepared in-situ in the mold immediately before the polymerization of polycaprolactam or other lactam began. As a result, longer molding cycles and increased use of initiator had to be tolerated when utilizing these polymeric initiators. Moreover, formulation difficulties were more prevalent since the initiator could not be added directly but rather had to be prepared in-situ. With the use of the claimed process, polymeric initiators can now be prepared and isolated. Thus when molding is commenced they can be added directly. Not only is the molding cycle shortened hence reducing energy and production costs but also less initiator is used and hence an additional materials cost savings is realized. Moreover, with the claimed process, a variety of polymeric initiators can be readily prepared tailored to the specific properties desired to be imparted to the polylactam. Therefore, the one step process of the claimed invention is energy and cost efficient and also results in increased productivity.

The invention will be further described in connection with the examples which follow. The examples are given as illustrative of the invention and are not to be construed as limiting it to their details.

EXAMPLE I

| Charge | Ingredients | Parts by Weight (grams) |
| --- | --- | --- |
| A | epsilon-caprolactam | 407.0 |
|   | acetic anhydride | 122.4 |
| B | acetic anhydride | 244.8 |
| C | EMPOL 1014[1] | 691.2 |

[1]An aliphatic dibasic acid commercially available from Emery Industries, Inc.

Charge A was placed in a two-liter flask and heated to a temperature of 110° C. until a liquid phase was obtained. The mixture was maintained at this temperature and Charge B was added. The aforesaid mixture was then maintained at reflux temperature for one hour followed by the addition of Charge C. This reaction mixture was heated in vacuo (200 millimeters of mercury) to a temperature of 210° C. and gradually reduced in pressure to 10 to 15 millimeters of mercury and stripped to remove acetic acid formed during reaction. The resultant product was the caprolactam imide of EMPOL 1014 dimer fatty acid.

EXAMPLE II

| Charge | Ingredients | Parts by Weight (grams) |
| --- | --- | --- |
| A | carboxyl-terminated polybutadiene acrylonitrile copolymer[1] | 2942 |
|   | acetic anhydride | 77 |
|   | epsilon-caprolactam | 254 |
| B | acetic anhydride | 153 |

[1]Commercially available from B. F. Goodrich as HYCAR 1300X8.

A reactor vessel was charged with (A) and heated to a temperature of 140° to 150° C. Charge (B) was then added over a one hour period while maintaining the same temperature. After the addition of (B) was completed, the reaction mixture was cooled to 60° C. The reaction mixture was then placed in vacuo (200 millimeters of mercury) and heated to 210° C. to remove the acetic acid which was evolved. When no further acetic acid evolution was apparent, the receiver was changed to prevent boiling of distillate during subsequent stripping. The reaction mixture was then cooled to 130° C. while reducing the pressure to 10 to 20 millimeters of mercury. The resultant lactam imide polymeric initiator had an acid number of 2.27 as determined by titrating with methanolic potassium hydroxide using phenol red indicator.

EXAMPLE III

This Example illustrates the preparation and molding of polycaprolactam utilizing an initiator composition of the present invention.

| Components of the Composition | Percentage of Components in Composition Less Reinforcement (weight percent) |
| --- | --- |
| Catalyst Side[A] | |
| Epsilon-caprolactam | 97.34 |
| Caprolactam magnesium bromide[1] as magnesium bromide (catalyst) | 2.66 |
| Initiator Side[B] | |
| Lactam imide terminated polybutadiene acrylonitrile polymeric initiator[2] | 50 |
| Polymeric initiator precursor[3] | 14 |
| Epsilon-caprolactam | 36 |
| 1/16 inch milled fiberglass reinforcement[4] | 10 percent by weight on resin mix |
| 1/64 inch treated flaked glass reinforcement[5] | 10 percent by weight on resin mix |

[A]The catalyst side was a mixture of 83.33 percent free epsilon-caprolactam and 16.67 percent caprolactam magnesium bromide catalyst concentrate.
[B]The initiator side was prepared by initially charging the lactam to a reactor vessel and heating it in vacuo for forty minutes at 85° C. To this melted caprolactam was added the polymeric initiator precursor and the lactam imide terminated polybutadiene acrylonitrile polymeric initiator. Heating was continued in vacuo for an additional 120 minutes at a temperature of 105° C. The resultant reaction mixture contained epsilon-caprolactam, lactam imide terminated polybutadiene acrylonitrile polymeric initiator, and polymeric polyether initiator with terminal ureimide groups. A ureimide group for the purposes of this application is

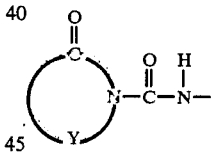

[1]This catalyst concentrate was prepared from 450 parts by weight of epsilon-caprolactam, 1700 parts by weight of cyclohexane, and 274 parts by weight of ethyl magnesium bromide (2.9 M in ether). The epsilon-caprolactam was agitated together with the cyclohexane until a dispersion was formed. Subsequently, the ethyl magnesium bromide was added in 20 milliliter aliquots at such a rate that the reaction temperature was maintained below 45° C. After each aliquot addition, the mixture was placed in vacuo for fifteen minutes. After the final aliquot addition, the cyclohexane was removed in vacuo leaving the caprolactam magnesium bromide as a white pulverulent residue.
[2]Prepared in Example I, above.
[3]This polymeric initiator precursor was prepared from 91.88 percent by weight of PLURONIC L-121 (a hydroxyl-terminated poly(oxyalkylene) derivative of propylene glycol commercially available from BASF-Wyandotte Corp.), 8.12 percent by weight of isophorone diisocyanate, and a trace amount (about 0.02 percent by weight) of dibutyltin dilaurate.
[4]This 1/16 inch milled fiberglass is commercially available from Owens-Corning Fiberglas Corp. as 737AA.
[5]This flaked glass reinforcement was prepared by slurrying commercially available 1/64 inch flaked glass (available from Owens Corning Fiberglas Corp.) in a solution of gamma-aminopropyltriethoxysilane and methanol followed by oven drying.

At the time of molding, 100 grams of the catalyst side were weighted into a vessel containing 100 grams of the initiator side, which had been mixed with 25.0 grams of milled fiberglass and 25.0 grams of flaked glass reinforcement. These component mixtures were stirred together for a period of about 30 seconds, poured into the mold, and cured for three minutes at a temperature of 150° C. The molded panel was then removed from the mold. The panel cured well, and exhibited excellent stiffness, surface quality and resistance to water absorption.

Although the invention has been described with specific references and specific details of embodiments thereof, it is to be understood that it is not intended to be so limited since changes and alterations therein may be made by those skilled in the art which are within the full intended scope of this invention as defined by the appended claims.

What is claimed is:

1. A process for preparing a lactam imide with comprises reacting together a lactam, a non-volatile carboxyl group-containing material, and an anhydride of a volatile carboxylic acid, with the proviso that an appreciable amount of non-volatile carboxyl group-containing material and volatile carboxylic acid which is generated as the anhydride reacts are both present in the reaction mixture at the same time.

2. The process of claim 1 wherein the lactam monomer is represented by the following structural formula:

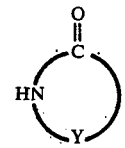

wherein Y is a $C_3$ to $C_{12}$ alkylene radical.

3. The process of claim 2 wherein the lactam monomer is epsilon-caprolactam.

4. The process of claim 1 wherein the anhydride of a volatile carboxylic acid contains at least four carbon atoms.

5. The process of claim 4 wherein the anhydride is acetic anhydride.

6. The process of claim 1 wherein the non-volatile carboxyl group-containing material is a monocarboxylic acid having at least four carbon atoms.

7. The process of claim 1 wherein the non-volatile carboxyl group-containing material is a polycarboxylic acid containing at least two carbon atoms.

8. The process of claim 1 wherein the non-volatile carboxyl group-containing material is a carboxyl group-containing polymer having an end group calculated molecular weight of at least 300.

9. The process of claim 8 wherein the carboxyl group-containing polymer is carboxyl group-terminated polybutadiene.

10. The process of claim 8 wherein the carboxyl group-containing polymer is a carboxyl group-terminated butadiene acrylonitrile copolymer.

* * * * *